United States Patent [19]

Olah

[11] Patent Number: 4,465,893

[45] Date of Patent: * Aug. 14, 1984

[54] OXIDATIVE CONDENSATION OF NATURAL GAS OR METHANE INTO GASOLINE RANGE HYDROCARBONS

[76] Inventor: George A. Olah, 2252 Gloaming Way, Beverly Hills, Calif. 90210

[*] Notice: The portion of the term of this patent subsequent to May 8, 2001 has been disclaimed.

[21] Appl. No.: 410,131

[22] Filed: Aug. 25, 1982

[51] Int. Cl.$^3$ ............................................... C07C 3/44
[52] U.S. Cl. .................................... 585/709; 585/400; 585/500; 585/700; 585/723; 585/732; 585/943; 502/224
[58] Field of Search ............... 585/415, 942, 945, 709, 585/711, 717, 721, 723, 724, 730, 732; 502/224

[56] References Cited

U.S. PATENT DOCUMENTS

| | | | |
|---|---|---|---|
| 3,636,129 | 1/1972 | Parker et al. | 585/709 |
| 3,678,120 | 7/1972 | Bloch | 585/730 |
| 3,809,728 | 5/1974 | Kemp et al. | 585/724 |
| 3,852,371 | 12/1974 | Kemp | 585/724 |
| 3,960,764 | 6/1976 | Bernard et al. | 585/730 |
| 3,979,476 | 9/1976 | Kemp | 585/724 |
| 4,025,577 | 5/1977 | Siskin et al. | 585/724 |
| 4,035,286 | 7/1977 | McCauley et al. | 585/717 |
| 4,044,069 | 8/1977 | Bernard et al. | 585/730 |
| 4,065,381 | 12/1977 | Say et al. | 585/730 |
| 4,162,233 | 7/1979 | Kremer | 585/942 |

FOREIGN PATENT DOCUMENTS 2372133  11/1976  France ............................... 585/724

*Primary Examiner*—Delbert E. Gantz
*Assistant Examiner*—A. Pal
*Attorney, Agent, or Firm*—Pennie & Edmonds

[57] ABSTRACT

This invention relates to a new process for the direct conversion of natural gas or methane into gasoline range hydrocarbons (i.e., synthetic transportation fuels or lower olefins) via catalytic condensation using superacid catalysts.

13 Claims, No Drawings

OXIDATIVE CONDENSATION OF NATURAL GAS OR METHANE INTO GASOLINE RANGE HYDROCARBONS

TECHNICAL FIELD

This invention relates to the direct conversion of natural gas or methane into gasoline-range hydrocarbons (i.e., synthetic transportation fuels or lower olefins) via catalytic condensation using superacid catalysts.

BACKGROUND ART

The present state of art for production of synthetic fuels from either coal or natural gas (the two major possible raw materials) involves initial production of synthesis gas which is then either converted directly to hydrocarbons (Fischer-Tropsch) or converted first to methyl alcohol, which subsequently is converted into hydrocarbons (Mobil process):

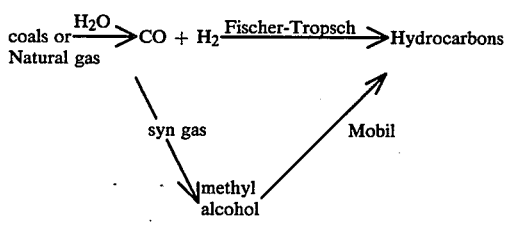

The Fischer-Tropsch process, although proven commercially, is not the most economically desirable process for the future due to its two very energetic steps and unsuitable product composition. The Mobil process is capable of producing gasoline-range hydrocarbons and aromatics relatively free of heavies, but suffers from the disadvantageous economics of first producing synthesis gas, which is then converted into methyl alcohol, which in turn is converted into hydrocarbons.

My discovery follows an independent and new route by utilizing methane (or natural gas) as the basic raw material. Methane as natural gas or even a biological "deep methane" is expected to be available well into the 2000's, and, if not utilized exclusively as an energy source but rather for transportation fuels and as a chemical raw material source, could last much longer. Furthermore, coal can be readily converted into methane by methanation or by in-situ gasification, thus avoiding difficulties in mining and transporting coal. Further, alternate sources of methane, such as the biological conversion of biomass (sewage recycling, utilization of plant life on land and sea [algae or kelp farming of the sea] with subsequent off shore conversion allowing the piping of methane to land), are becoming available. If in the future as cheaper atomic or fusion energy becomes available, during off-peak periods, these plants could become producers of aluminum carbide which, upon hydrolysis, gives methane (with ethane and ethylene as by-products.) The conversion of methane to higher hydrocarbons thus represents a viable new alternative to synthetic hydrocarbon processes.

The oligocondensation of methane was discovered by Olah et al., *Journal of the American Chemical Society*, 90, 2726 (1968), using exceedingly strong acid systems, the so-called "superacids", comprising a mixture of fluorosulfuric acid and antimony pentafluoride ("magic acid"), a mixture of hydrogen fluoride and antimony pentafluoride, or related superacids. Superacids have a Hammett acidity function $H_o$ less than $-11.9H_o$, the value for 100 percent sulfuric acid. However, yields were extremely low and the superacid was reductively depleted, rendering the process impractical on a commercial scale.

Alkane-alkene condensations (alkylations) such as that of isobutane with isobutylene to produce $C_8$ alkylate is well known in the petrochemical industry. Olah reported first the alkylation of alkanes with alkyl cations, generated in superacidic media [J.Am.Chem.Soc., 95, 4939–4952 (1973)].

The condensation (polymerization) of methane and olefins represents a special problem and for a long time, methane was considered to be inert to usual acid catalyzed electrophilic reactions. The work of Olah on the superacid catalyzed reactivity of methanes opened up the possibility for such reactions. D. T. Roberts, Jr. and L. E. Calihan [J.Macronol.Sci-Chem., A7 (8) pp. 1641–1646 (1973)] reported that mixtures of methane and olefins (ethylene, propylene, etc.) polymerized in an autoclave at room temperature over a liquid magic acid ($HSO_3F/SbF_5$) catalyst to give oily oligomers with molecular weight of 100 to 700. Conversions were low (in the case of methane and ethylene, 5%) and under the used liquid phase conditions with long contact times (generally 24 hours) the olefin itself tended to polymerize on its own. Subsequently using another liquid superacid catalyst, hydrogen fluoride-tantalum pentafluoride, Siskin carried out the alkylation of methane wih ethylene in a pressurized flow system [J.Am.Chem. Soc., 98, 5413 (1976)]. No yields or conversions were given and again the liquid phase reaction conditions were considered to substantially limit practical application of the reaction.

DESCRIPTION OF THE INVENTION

In sharp contrast to previous practice, I have now found a practical way to convert methane into gasoline-range hydrocarbons (synthetic transportation fuels) by condensing a gaseous feed comprising methane or natural gas in the presence of a solid or supported superacid.

The condensation of methane into higher hydrocarbons must overcome the unfavorable endothermic thermodynamics of such individual steps as noted below:

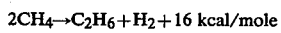

$$2CH_4 \rightarrow C_2H_6 + H_2 + 16 \text{ kcal/mole}$$

In order to overcome this difficulty, it is advantageous to oxidatively remove hydrogen. The removal of hydrogen has now been discovered to be possible in two ways.

In one embodiment of the invention higher hydrocarbons are produced when natural gas or methane is condensed in a single step in the presence of a suitable oxidant over the solid or supported superacid catalyst.

In an alternative embodiment of the invention methane or natural gas is condensed in admixture with at least one lower olefin in the $C_2$ to $C_4$ range and/or with acetylene, in the presence of the solid or supported superacid catalyst. Such admixtures are readily obtained for instance by the dehydrogenation of natural gas to a mixture of methane and lower olefins, or by the thermal treatment of natural gas to form a mixture of methane and acetylene.

The useful catalysts can be selected from higher valency Lewis Acid halides of metals of Groups IV, V and VI of the Periodic Table such as tantalum pentafluoride, niobium pentafluoride, antimony pentafluoride and the like, supported on a suitable chalconite carrier, preferentially in its fluorinated form such as fluorinated alumina, or the like, or on a graphite, fluorinated graphite or aluminum trifluoride carrier.

As noted in Olah, G. A. "Friedel-Crafts Chemistry," N.Y., Wiley-Interscience, 1973. p. 343-344, the elements of Group VIA such as oxygen, sulfur, selenium or tellurium, have been called "chalcogens", and compounds containing these elements are called "chalconites", "chalcogenides" or "chalcides." A variety of solid oxides and sulfides, especially those comprising alumina, and mixtures of alumina, either natural or synthetic, in which other oxides such as chromia, magnesia, molybdena, thoria, tungstic oxide, zirconia, etc., may also be present, as well as sulfides of molybdenum are useful chalcide carriers. Many naturally occurring compositions exist for use as the carrier including: bauxite, floridin, Georgia clay, and other natural aluminosilicates.

Synthetic chalcides, other than those of the silica-alumina type, representative of the chalcide carriers are: $BeO$, $Cr_2O_3$, $P_2O_5$, $ThO_2$, $TiO_2$, $Al_2(SO_4)_3$ (which may be regarded as $Al_2O_3 3SO_3$), $Al_2O_3 Cr_2O_3$, $Al_2O_3$, $Fe_2O_3$, $Al_2O_3 CoO$, $Al_2O_3 MnO$, $Al_2O_3 V_2O_3$, $Al_2O_3 Mo_2O_3$, $Cr_2O_3 Fe_2O_3$, $MoS_2$, and $MoS_3$.

The chalcide supports should be physically and chemically stable. Under the reaction conditions, they are generally catalytically active at only higher temperatures, as their acidity is not great enough to lead them to form stable complexes with unsaturated compounds, as do the aluminum halides, for example.

Useful catalysts can also be selected from superacidic conjugated acids composed of a strong Bronsted acid such as hydrogen fluoride, fluorosulfuric acid, perfluoroalkane-sulfonic acids of 1 to 18 carbon atom length, supported on a suitable solid carrier, or polymeric perfluorinated acids such as Nafion-H or copolymers of perfluorovinyl perfluorinated polymeric resin-sulfonic acids and the like, in conjunction with a suitable Lewis Acid fluoride, such as those of the metals of Groups IV, V and VI of the Periodic Table.

The solid or supported solid catalysts are used at temperatures between about 15° and 250° C. and pressures of about 1 to 150 or more atmospheres. The feed comprises methane alone, or mixtures which generally contain a substantial excess of methane, in mole ratios of 6 to 12:1 to olefins and/or acetylene, readily obtainable from pretreatment of natural gas by catalytic dehydrogenation or thermal reaction.

These condensations generally produce alkane mixtures, as well as cycloalkanes and aromatics of less than 12 carbons, but not olefins.

The first method involves the oxidative condensation of methane, in which an oxidizing agent, such as air, oxygen, oxygen-ozone mixture, sulfur, selenium, sulfur trioxide, nitrogen oxides, halogens (fluorine, chlorine, bromine, iodine) is utilized to remove hydrogen as noted below.

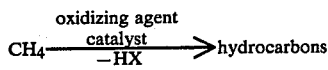

Oxidative condensation in the presence of air or oxygen gives water as by-product. Recovery of hydrogen is thus not feasible.

The oxidative condensation of methane with sulfur gives $H_2S$ as a by-product. It can be readily oxidized to recover sulfur or, alternatively, it was discovered that by combining a CO shift reaction over a supported molybdenum sulfide catalyst with catalytic or thermal decarbonylation of COS, it is possible to obtain hydrogen and regenerate sulfur, thus allowing the following condensation:

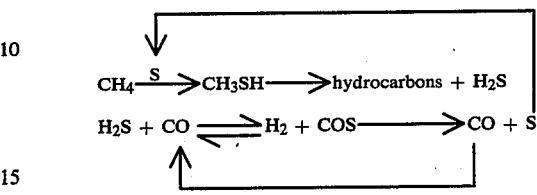

to proceed to hydrocarbons and hydrogen. This approach allows a methane condensation with the recovery of hydrogen, or is also applicable to hydrogen production from refinery gases, sour gas wells or coal desulfurization.

The oxidative condensation of methane can also be carried out with halogens as the oxidizing agents. Methane can be chlorinatively (brominatively, iodinatively) condensed under the reaction conditions. Initially, methyl chloride, bromide, or iodide are formed (or methyl fluoride, if the halogenation is carried out in the presence of HF) which are subsequently readily condensed into higher hydrocarbons. HCl, HBr or HI can be recycled via oxyhalogenation, whereas HF is reusable as such. The condensation reaction is preferably carried out at a temperature of about 50° to 250° C. and at a pressure of about 1 to 50 atmospheres.

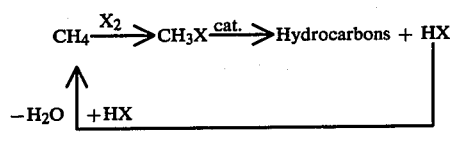

X = Cl, Br, I

The second method involves the dehydration of natural gas to a mixture of methane and lower olefins (ethylene, with some propylene and butenes) or, alternatively, its thermal treatment to form acetylene, (as well as ethylene) and condensing these mixtures in the presence of aforementioned solid superacid catalysts to hydrocarbons in the gasoline-range:

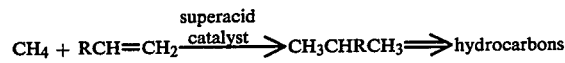

R = H, $CH_3 C_2H_5$ or,

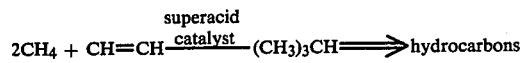

As lower olefins readily undergo themselves acid catalyzed condensations, their reactions with methane must be carried out under conditions where these self condensations can be minimized. This can be achieved utilizing a suitable excess of methane and preferentially premixing anhydrous hydrogen fluoride with the olefins which intermediately form alkyl fluorides, regenerating hydrogen fluoride in the alkylation reaction

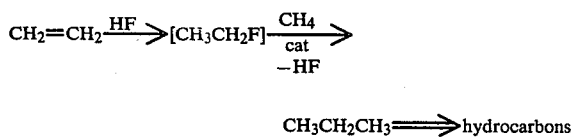

Illustrative of the invention are the following examples, set forth for the purpose of illustration only and not to be construed as limiting the scope of the invention in any matter. In the related Tables where product compositions are given, they have been normalized, even if not stated, to provide a total of 100% conversion, excluding unreacted methane which can be recycled.

EXAMPLE 1

Natural gas containing about 82% methane and 18% ethane, with some propane and butane, is subjected to conventional catalytic dehydrogenation (cracking), yielding, in addition to unreacted methane, an ethylene-propylene containing feed which after drying can be utilized directly in the condensation reaction. The obtained methane-ethylene feed (in about 90:10 ratio) containing some ethane, propylene, butylenes, which do not need to be separated, is reacted over a tantalum pentafluoride catalyst supported on fluoridated alumina (10% per weight), at a temperature of 70° C. in a continuous flow reactor. A 38% conversion per pass (based on reacted ethylene) is obtained with the following composition:

| Product composition | (%)[a] |
|---|---|
| $C_2H_6$ | 13.2 |
| $C_3H_8$ | 13.8 |
| $i\text{-}C_4H_{10}$ | 48.6 |
| $n\text{-}C_4H_{10}$ | 6.5 |
| $i\text{-}C_5H_{12}$ | 12.7 |
| $n\text{-}C_5H_{12}$ | 5.3 |

[a]methane excluded and normalized to 100%

EXAMPLE 2

A feed mixture consisting of about 88% methane and 10% acetylene was treated under the conditions of Example 1 over the supported tantalum pentafluoride at 70° C. in the continuous flow reactor. A 78% conversion per pass (based on feed acetylene) was obtained with the following product distribution:

| Product distribution | (%)[a] |
|---|---|
| $C_2H_6$ | 3.7 |
| $C_3H_8$ | 6.1 |
| $i\text{-}C_4H_{10}$ | 84.2 |
| $n\text{-}C_4H_{10}$ | <1 |
| $i\text{-}C_5H_{12}$ | 5.0 |
| $n\text{-}C_5H_{12}$ | <1 |

EXAMPLE 3

Under the conditions of Example 2, a feed mixture consisting of about 80% methane, 10% ethylene and 10% acetylene was passed through the supported tantalum pentafluoride catalyst at 70° C. A 68% conversion per pass was obtained with the following product composition:

| Product composition | (%)[a] |
|---|---|
| ethane | 22.5 |
| propane | 1.8 |
| butanes | 14.1 |
| pentanes | 39.6 |
| hexanes | 22.0 |

EXAMPLE 4

A 9:1 natural gas (consisting of about 90% methane and 10% ethane)-oxygen mixture was reacted at a pressure of 65 atom. at 120° C. over a 20% antimony pentafluoride deposited on fluorinated graphite. A 13% conversion was obtained. The hydrocarbon product contained 21 to 27% ethylene, 6 to 8% propane, 31–40% butanes, 11–16% pentanes, with the balance being oxygenated products.

EXAMPLE 5

Methane was reacted in the presence of sulfur in the ratio of 5:1 in the presence of the tantalum pentafluoride catalyst containing HF at 270° C. in a stainless steel pressure reactor. A 2 to 10% conversion to condensed saturated hydrocarbons is achieved depending on reaction time (1 to 24 hrs) with the following product composition.

| Product composition | (%)[a] |
|---|---|
| ethane | 38–50 |
| propane | 5–8 |
| butanes | 40–49 |
| pentanes | 5–15 |

EXAMPLE 6

Methane was reacted in the presence of sulfur in a ratio of 5:1 in the presence of antimony pentafluoride catalyst at 200° C. as in Example 5. A 3 to 15% conversion with similar produce composition was obtained.

EXAMPLE 7

Methane was reacted in the presence of selenium in a ratio of 5:1 in the presence of tantalum pentafluoride catalysts at 200° C. in a stainless steel pressure autoclave for six hours. A 3 to 16% conversion to condensed saturated hydrocarbons is achieved with the following typical product composition:

| Product composition | (%)[a] |
|---|---|
| ethane | 18–34 |
| propane | 2–5 |
| butanes | 34–48 |
| pentanes | 11–23 |
| hexanes | 6–19 |

EXAMPLE 8

A 2:1 methane-chlorine mixture was reacted over a perfluorinated resinsulfonic acid (Nafion-H) catalyst complexed with 20% tantalum pentafluoride at 185° C. in the previously utilized continuous flow reactor. 40% per pass conversion gave the following product composition:

| Product composition | (%)a |
|---|---|
| methyl chloride | 2 |
| methylene chloride | 7 |
| ethane | 3 |
| ethyl chloride | 40 |
| isobutane | 48 |

EXAMPLE 9

A 2:1 methane-chlorine mixture was reacted over a catalyst prepared by intercalating (immobilizing) 30% antimony pentafluoride onto graphite, at 120° C. Typical per pass conversions were 32% with product composition of

| Product composition | (%)a |
|---|---|
| methyl chloride | 37–58 |
| ethyl chloride | 1–4 |
| methylene chloride | 9–14 |
| isobutane | 25–48 |

EXAMPLE 10

In a pressure reactor, methane was reacted over a graphite catalyst intercalated with 30% antimony pentafluoride at 20° C. and 140 psi pressure. The reactor was initiated with anhydrous HF and a halogen (fluorine, chlorine). Initial methane conversion was 15 to 29% with the following typical hydrocarbon product composition (excluding halomethanes):

| Product composition | (%)a |
|---|---|
| ethane | 8–23 |
| propane | 3–8 |
| butanes | 32–48 |
| pentanes | 11–28 |
| hexanes | 6–15 |

Conversion decreases with time as activity decreases during the reaction. It can, however, be restored by treating the system again with anhydrous hydrogen fluoride containing fluorine or chlorine as the oxidizing agent. The reaction is advantageously carried out using alternating parallel reactors, in one of which the reaction is carried out, while in the other system is regenerated.

EXAMPLE 11

Methane was reacted over a catalyst, which was 20% tantalum pentafluoride supported on anhydrous aluminum fluoride, in a pressure reactor at 20° C. and 140 psi. The reaction is initialed with anhydrous hydrogen fluoride and a halogen (fluorine or chlorine). The reaction was carried out and the system reactivated as in Example 10. Initial methane conversion was 12 to 19% with the following typical hydrocarbons product composition (excluding halomethanes):

| Product composition | (%)a |
|---|---|
| ethane | 8–19 |
| propane | 1–5 |
| butanes | 46–58 |
| pentanes | 12–27 |
| hexanes | 5–17 |

EXAMPLE 12

Methane was reacted over a solid, superacidic catalyst, prepared by intercalating graphite with 30% antimony pentafluoride, with ethylene in the presence of excess hydrogen fluoride in a manner that ethylene is first contacted with hydrogen fluoride converting it into ethyl fluoride, thus avoiding presence of excess free ethylene. This can be achieved under conditions of Example 10 utilizing alternating parallel reactors. Typical hydrocarbon product compositions are:

| Product composition | (%)a |
|---|---|
| ethane | 10–15 |
| propane | 2–8 |
| butanes | 41–48 |
| pentanes | 13–21 |
| hexanes | 10–18 |

I claim:

1. A process for the heterogeneous gas-phase conversion of methane into gasoline-range hydrocarbons by condensing a gaseous feed comprising methane or natural gas in the presence of a solid superacid catalyst.

2. A process according to claim 1 wherein the gaseous feed is condensed in the presence of an oxidizing agent selected from air, oxygen, oxygen-ozone mixtures, sulfur, selenium, sulfur trioxide, nitrogen oxides and halogens.

3. A process according to claim 1 wherein the solid superacid catalyst is selected from higher valency Lewis Acid halides of metals of groups IV, V or VI of the Periodic Table, supported on a carrier.

4. A process according to claim 3 wherein the higher valency Lewis Acid halide is selected from tantalum pentafluoride, niobium pentafluoride and antimony pentafluoride.

5. A process according to claim 3 wherein the carrier is a chalconite, graphite, fluorinated graphite or aluminum fluoride.

6. A process according to claim 5, wherein the chalconite carrier is fluoridated.

7. A process according to claim 1 wherein the solid superacid catalyst is composed of a strong Bronsted acid component selected from hydrogen fluoride, fluorosulfuric acid, perfluoroalkanesulfonic acids of 1 to 18 carbon atoms deposited on a suitable carrier, perfluorinated polymeric resinsulfonic acids copolymers of perfluorovinylsulfonic acid and tetrafluoroethylene or trifluorochloroethylene complexed with a Lewis Acid fluoride of metal of groups IV, V or VI of the Periodic Table.

8. A process according to claim 1 wherein the solid superacid catalyst is antimony pentafluoride deposited on graphite or fluorinated graphite.

9. A process according to claim 1 wherein the solid superacid catalyst is tantalum pentafluoride deposited on aluminum trifluoride, fluoridated alumina, graphite or fluorinated graphite.

10. A process according to claim 1 wherein the gaseous feed is condensed at a temperature between about 15 and 250 degrees centigrade and a pressure of about 1 to 150 atmospheres.

11. A process according to claim 1 wherein the gaseous feed is condensed at a temperature between about 50 and 250 degrees centigrade and a pressure of about 1 to 150 atmospheres.

12. A process according to claim 1 wherein the methane or natural gas is condensed in admixture with at least one lower olefin in the $C_2$ to $C_4$ range.

13. A process according to claim 1 wherein the methane or natural gas is condensed in admixture with acetylene.

* * * * *